United States Patent
Ewers et al.

(10) Patent No.: US 10,960,163 B2
(45) Date of Patent: Mar. 30, 2021

(54) APPARATUS, SYSTEMS, AND METHODS FOR IMPROVED TREATMENT OF OBSTRUCTIVE SLEEP APNEA

(71) Applicant: Fresca Medical Inc., San Clemente, CA (US)

(72) Inventors: Richard Ewers, Fulterton, CA (US); Kevin Chen, Palos Verdes Estates, CA (US); Andrew Dominguez, San Clemente, CA (US)

(73) Assignee: Fresca Medical Inc., San Clemente, CA (US)

( * ) Notice: Subject to any disclaimer, the term of this patent is extended or adjusted under 35 U.S.C. 154(b) by 392 days.

(21) Appl. No.: 15/690,195

(22) Filed: Aug. 29, 2017

(65) Prior Publication Data
US 2018/0064899 A1    Mar. 8, 2018

Related U.S. Application Data

(60) Provisional application No. 62/532,240, filed on Jul. 13, 2017, provisional application No. 62/465,905, (Continued)

(51) Int. Cl.
*A61M 16/06* (2006.01)
*A61M 16/08* (2006.01)
(Continued)

(52) U.S. Cl.
CPC .... *A61M 16/0666* (2013.01); *A61M 16/0616* (2014.02); *A61M 16/0683* (2013.01); (Continued)

(58) Field of Classification Search
CPC .......... A61M 16/0066; A61M 16/0616; A61M 16/0666; A61M 16/0683; A61M 16/0816; (Continued)

(56) References Cited

U.S. PATENT DOCUMENTS 3,419,031 A    12/1968 Hesse
3,556,122 A    1/1971 Laerdal
(Continued)

FOREIGN PATENT DOCUMENTS

WO    1992/020392 A1    11/1992

OTHER PUBLICATIONS

International Search Report and Written Opinion issued in PCT/US2017/049404 dated Dec. 27, 2017 (10 pages).

*Primary Examiner* — Samchuan C Yao
*Assistant Examiner* — Nathan M Le
(74) *Attorney, Agent, or Firm* — Manuel de la Cerra

(57) ABSTRACT

A nasal pillow system for treating sleep apnea is disclosed that may include a nasal pillow. The pillow has a cavity wall that defines a cavity, and two nasal interface structures connected to and extending away from the cavity wall. The nasal interface structures are in fluid communication with the cavity. Each nasal interface structure includes a conical nasal interface, a cylindrical trunk structure connected to conical nasal interface, and an annular relief pocket connected to the cylindrical trunk structure and to the cavity wall. The connection between the annular relief pocket and the cavity wall defines substantially a plane, and a first portion of the annular relief pocket extends away from the plane while a second portion extends towards the plane.

10 Claims, 15 Drawing Sheets

Related U.S. Application Data filed on Mar. 2, 2017, provisional application No. 62/382,980, filed on Sep. 2, 2016, provisional application No. 62/382,988, filed on Sep. 2, 2016.

(51) Int. Cl.
*A61M 16/20* (2006.01)
*A61M 16/00* (2006.01)

(52) U.S. Cl.
CPC ..... *A61M 16/0816* (2013.01); *A61M 16/0066* (2013.01); *A61M 16/0875* (2013.01); *A61M 16/20* (2013.01); *A61M 2205/42* (2013.01); *A61M 2210/0618* (2013.01)

(58) Field of Classification Search
CPC .......... A61M 16/0875; A61M 16/0672; A62B 23/06
See application file for complete search history.

(56) References Cited

U.S. PATENT DOCUMENTS

| | | | |
|---|---|---|---|
| 3,978,878 A | 9/1976 | Rudolph | |
| 4,239,038 A | 12/1980 | Holmes | |
| 4,373,520 A | 2/1983 | Arbique | |
| 4,428,392 A | 1/1984 | Jones et al. | |
| 4,782,832 A | 11/1988 | Trimble et al. | |
| 5,002,050 A | 3/1991 | McGinnis | |
| 5,005,568 A | 4/1991 | Loescher et al. | |
| 5,647,355 A | 7/1997 | Starr et al. | |
| 5,687,715 A | 11/1997 | Landis et al. | |
| 6,306,114 B1 | 10/2001 | Freeman et al. | |
| 6,431,172 B1* | 8/2002 | Bordewick | A61M 16/0666 128/206.11 |
| 6,626,177 B1 | 9/2003 | Ziaee | |
| 7,900,635 B2 | 3/2011 | Gunaratnam et al. | |
| 8,136,525 B2* | 3/2012 | Lubke | A61M 16/0816 128/206.28 |
| 8,312,881 B2 | 11/2012 | Gunaratnam et al. | |
| 8,573,201 B2* | 11/2013 | Rummery | A61M 16/06 128/200.24 |
| 8,636,007 B2 | 1/2014 | Rummerty et al. | |
| 8,800,563 B2* | 8/2014 | Doherty | A61M 16/0683 128/207.11 |
| 9,144,653 B2 | 9/2015 | Chalvignac | |
| 2002/0170562 A1 | 11/2002 | Lurie et al. | |
| 2002/0195105 A1 | 12/2002 | Blue et al. | |
| 2004/0099266 A1 | 5/2004 | Cross et al. | |
| 2006/0137690 A1* | 6/2006 | Gunaratnam | A61M 16/0633 128/206.11 |
| 2006/0237017 A1* | 10/2006 | Davidson | A61M 16/06 128/205.25 |
| 2008/0078395 A1* | 4/2008 | Ho | A61M 16/208 128/205.24 |
| 2009/0032022 A1 | 2/2009 | Ho et al. | |
| 2009/0044808 A1* | 2/2009 | Guney | A61M 16/0666 128/206.24 |
| 2009/0320851 A1* | 12/2009 | Selvarajan | A61M 16/0683 128/207.13 |
| 2010/0024824 A1* | 2/2010 | Chalvignac | A61M 16/206 128/205.24 |
| 2010/0229868 A1* | 9/2010 | Rummery | A61M 16/06 128/205.25 |
| 2011/0253147 A1* | 10/2011 | Gusky | A61M 16/206 128/207.18 |
| 2012/0138061 A1* | 6/2012 | Dravitzki | A61M 16/0683 128/205.25 |
| 2012/0204870 A1* | 8/2012 | McAuley | A61M 16/0616 128/203.12 |
| 2012/0318274 A1* | 12/2012 | Ho | H04M 16/0666 128/207.18 |
| 2012/0325218 A1* | 12/2012 | Brambilla | A61M 16/0875 128/205.25 |
| 2013/0102916 A1* | 4/2013 | Colbaugh | A61B 5/4818 600/533 |
| 2014/0276177 A1* | 9/2014 | Brambilla | A61M 16/0666 600/543 |
| 2014/0305431 A1* | 10/2014 | Holley | A61M 16/0003 128/201.13 |
| 2015/0040907 A1* | 2/2015 | Hakim | A63B 23/18 128/205.24 |
| 2016/0030229 A1 | 2/2016 | Goldschmidt | A61M 16/201 128/847 |
| 2016/0082209 A1* | 3/2016 | Witt | A61M 16/0666 128/204.23 |

* cited by examiner

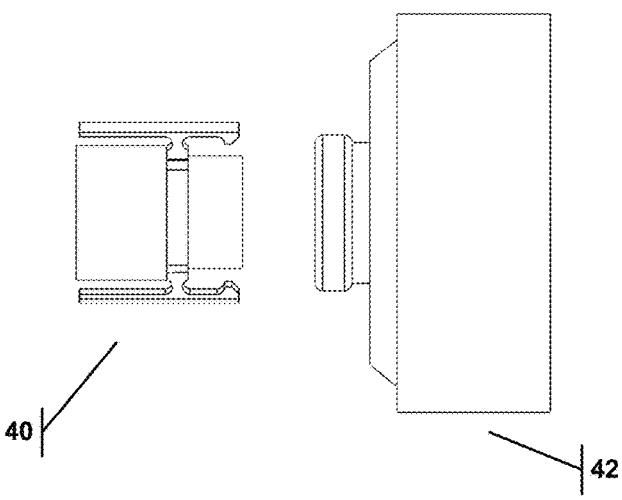
FIG. 2C
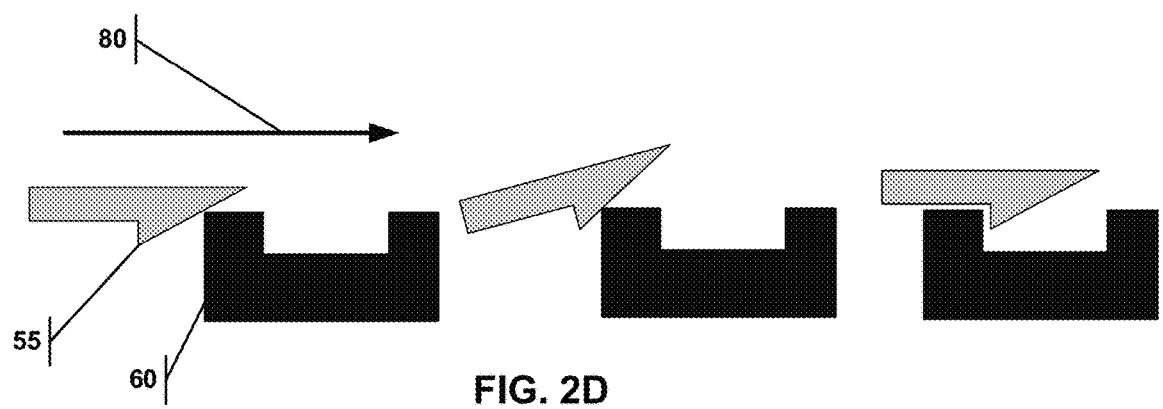
FIG. 2D
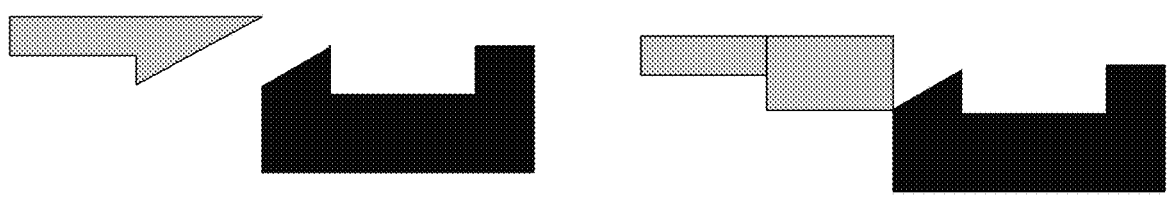
FIG. 2E
FIG. 2F

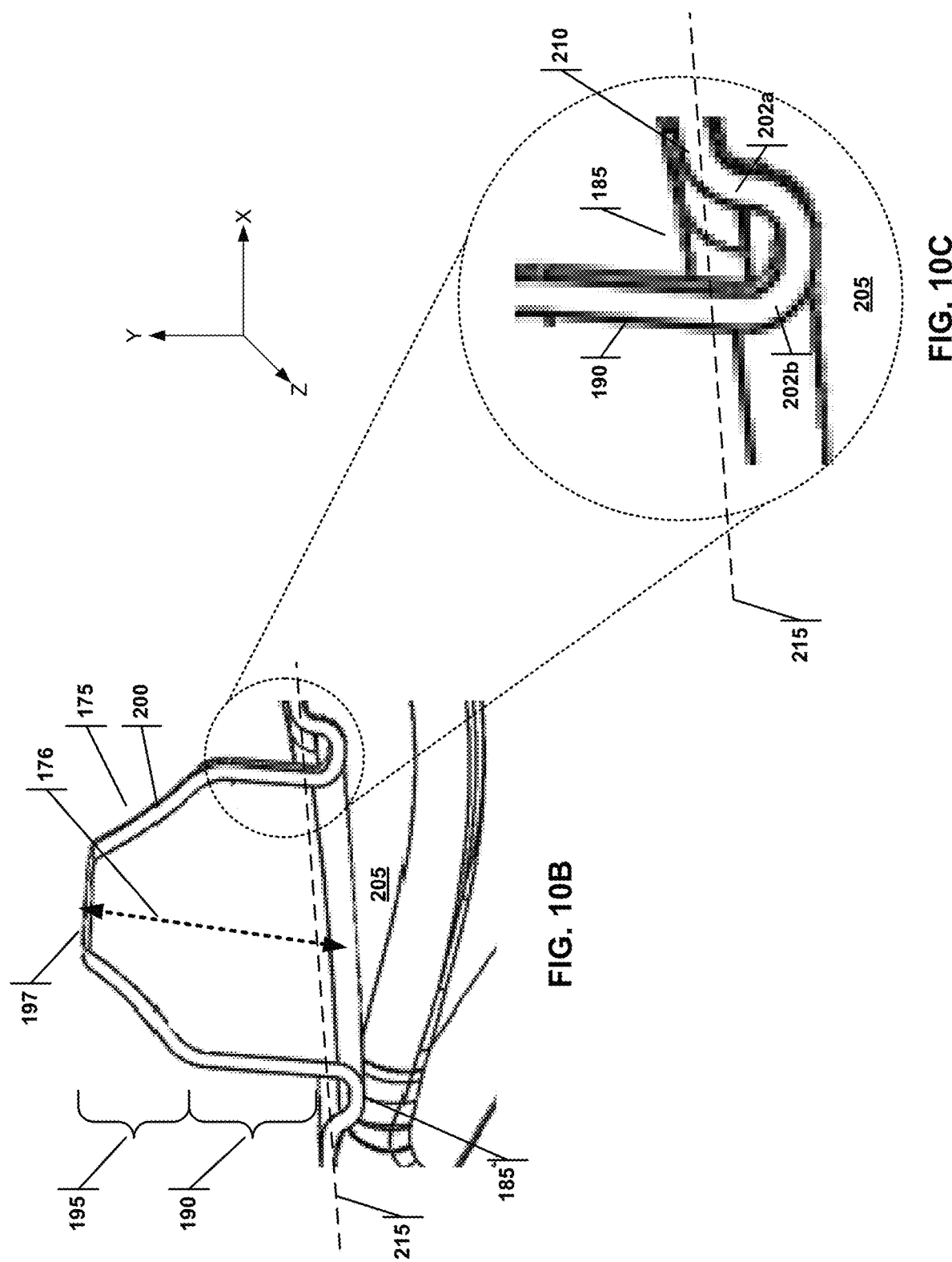

APPARATUS, SYSTEMS, AND METHODS FOR IMPROVED TREATMENT OF OBSTRUCTIVE SLEEP APNEA

2.0 RELATED APPLICATIONS

This application claims priority as the non-provisional of U.S. Provisional Application No. 62/382,988 filed Sep. 2, 2016, titled "Nasal Pillow and Head Gear for Use with CPAP Treatment", the non-provisional of U.S. Provisional Application No. 62/382,980 filed on Sep. 2, 2016, titled "Dual Rotatable Hose for Use with CPAP Treatment," the non-provisional of U.S. Provisional Application No. 62/465,905 filed on Mar. 2, 2017, titled "Sound Mitigation/Flow Optimization in a Valved Obstructive Sleep Apnea Treatment Mask", and the non-provisional of U.S. Provisional Application No. 62/532,240 filed Jul. 13, 2017, titled "Sleep Apnea Treatment System and Improvements Thereto", all of which are hereby incorporated by reference in their entirety.

In addition, this application is related by common inventors and by a common assignee to U.S. patent application Ser. No. 13/860,926, filed Apr. 11, 2013, titled "Sleep Apnea Device," U.S. Provisional Application Ser. No. 61/623,855, filed Apr. 13, 2012, titled "Sleep Apnea Device," U.S. Provisional Application Ser. No. 61/775,430, filed Mar. 8, 2013, titled "Sleep Apnea Device," U.S. Provisional Application No. 61/823,553, filed May 15, 2013, titled "Sleep Apnea Device," U.S. Provisional Application No. 61/838,191, filed Jun. 21, 2013, titled "Sleep Apnea Device," U.S. Provisional Application No. 61/962,501, filed Nov. 8, 2013, titled "Sleep Apnea Device," U.S. Provisional Application No. 61/909,956, filed Nov. 27, 2013, titled "Sleep Apnea Device," U.S. Provisional Application No. 61/927,355, filed Jan. 14, 2014, titled "Valve with Pressure Feedback," U.S. Provisional Application No. 62/134,506 filed Mar. 17, 2015 titled "Valve with Pressure Feedback Draft Provisional Application," U.S. Provisional Application No. 62/163,601, filed May 19, 2015, titled "Airflow Generator with Delayed Onset", U.S. Provisional Application No. 62/184,787 filed Jun. 25, 2015, titled "Sleep Apnea Device," U.S. Provisional Application No. 62/239,146 filed Oct. 8, 2015, titled "Sleep Apnea Device," U.S. patent application Ser. No. 14/930,284, filed Nov. 2, 2015, titled "Apparatus, System and Methods for Treating Obstructive Sleep Apnea", U.S. Provisional Application No. 62/246,339 filed Oct. 26, 2015, titled "Venting of a Valved CPAP Mask to Create a Comfortable Breathing Sensation", U.S. Provisional Application No. 62/246,489 filed Oct. 26, 2015, titled "Managing Sleep Apnea with Pulse Oximeters and With Additional Assessment Tools", U.S. Provisional Application No. 62/246,328 filed Oct. 26, 2015, titled "Novel Low Flow Technology Designed to Meet CPAP Efficacy", U.S. Provisional Application No. 62/246,477 filed Oct. 26, 2015, titled "Composite Construction Air Delivery Hose for USE with CPAP Treatment", U.S. Provisional Application No. 62/275,899 filed Jan. 7, 2016, titled "Valved Mask To Reduce and Prevent Snoring", and U.S. Provisional Application No. 62/311,804 filed Mar. 22, 2016, titled "Improvements to Sleep Apnea Machine", all of which are hereby incorporated by reference in their entirety.

Disclosed in this application are features intended to be used in conjunction with the CPAP methods and devices described in the aforementioned applications.

1.0 TECHNICAL FIELD

The present invention is related to medical systems, devices, and methods. More specifically, the invention is related to systems, devices and methods for treating obstructive sleep apnea or snoring.

2.0 BACKGROUND

Obstructive sleep apnea (OSA) is a common medical disorder that can be quite serious. It has been reported that approximately one in twenty-two Americans (about 12,000,000 people) suffer from OSA, and many cases go undiagnosed. Chronic fatigue has long been recognized as the hallmark of OSA, but more recently, large clinical studies have shown strong links between OSA and strokes and between OSA and death.

Obstructive sleep apnea is a condition in which the flow of air pauses or decreases during breathing while one is asleep, because the airway has become narrowed, blocked, or floppy. A pause in breathing is called an apnea episode, while a decrease in airflow during breathing is called a hypopnea episode. Almost everyone has brief apnea or hypopnea episodes while they sleep. In OSA, however, apnea episodes occur more frequently and last longer than in the general population. OSA has become an increasingly costly medical condition in recent years, as the disorder is more prevalent in obese people, and obesity has become significantly more prevalent. Unfortunately, the currently available options for treating OSA are not ideal.

A person with OSA usually begins snoring heavily soon after falling asleep. Often, the snoring gets louder. The snoring is then interrupted by a long silent period, during which there is no breathing. This is followed by a loud snort and a gasp as the person attempts to breathe. This pattern repeats. Many people wake up unrefreshed in the morning and feel sleepy or drowsy throughout the day. This is called excessive daytime sleepiness (EDS). People with sleep apnea may act grumpy or irritable, be forgetful, fall asleep while working, reading, or watching TV, feel sleepy or even fall asleep while driving, or have hard-to-treat headaches. OSA sufferers may also experience depression that becomes worse, hyperactive behavior (especially in children), or leg swelling (if severe).

The most widely used therapy for OSA is Continuous Positive Airway Pressure (CPAP). A CPAP system typically consists of a mask fitting in or over the nose or nose and mouth, an air pressurizing console (or blower) and a hose connecting the two (typically a six-foot long hose with a 20 mm diameter bore). CPAP works by pressurizing the upper airway throughout the breathing cycle, essentially inflating the airway to keep it open and thus creating what is sometimes referred to as a "pneumatic splint." This flow is set at a pressure that has been predetermined through medical testing to be appropriate to create a pneumatic splint in the patient's airway. This prevents airway collapse and allows the patient to breathe without obstruction.

Typically, air flow for CPAP ranges from 100-200 L/min at a corresponding pressure range of 4-20 CM-H2O. This high flow rate makes breathing feel quite uncomfortable for many patients and requires a large and cumbersome hose measuring about 22 mm (~0.86") in diameter. Additionally, the high required flow rates of CPAP often cause discomfort during exhalation due to increased resistance, as well as nasal dryness, dry mouth, ear pain, rhinitis, abdominal bloating and/or headaches. Typically, a patient requires a humidification machine to prevent some of the side effects of the high flow rate.

Because of these shortcomings, the overwhelming problem of CPAP is poor patient compliance, with over half of all patients who try CPAP stop using it. Patients dislike the side effects mentioned above, as well as having to wear an uncomfortable, claustrophobic mask, being tethered to a pressurizing console, the noise of the console, traveling with a bulky device, and a loss of personal space in bed.

Therefore, it would be advantageous to have improved systems, devices and methods for treating OSA and snoring. Ideally, such systems, devices and methods would be less cumbersome than currently available CPAP systems, to improve patient compliance. Also ideally, such systems, devices and methods would provide some of the advantages of an expiratory pneumatic splint. At least some of these objectives were met by the embodiments described in references listed above and incorporated herein by reference.

While these references are an important improvement over the state of the art, it would be advantageous to improve upon these systems by making the system simpler and more compact in design, simpler to use, and more robust.

3.0 SUMMARY

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

Provided in various example embodiments is a hose connection system for treating sleep apnea that may include a hinged lever hose connector with a hose portion and a blower box/mask portion. The hose portion may contain an annular structure connected to a hook lever by way of a fulcrum, the hook lever has a hook. The blower box/mask portion has a grooved collar with an outer surface and a groove disposed of on this surface. The connector has two states: a engaged state where the hook is disposed of in the groove, thereby connecting the hose portion to the blower box/mask portion; and a disengaged state where the hook lever is rotated about the fulcrum, thereby moving the hook away from the groove allowing the hose portion to be disconnected from the blower box/mask portion. In the engaged state, the hook can travel along the groove such that the annular structure can rotate relative to the blower box/mask portion.

The hose portion may include more than one hook lever. The hook and an edge of the grooved collar may be wedge-shaped. The hook lever may include a disengagement surface on the opposite side of the fulcrum from the hook, such that the connector may be placed in the disengaged state by applying force to the disengagement surface. A hose may be connected to the hose portion and to a blower box, a mask, a nasal pillow or valve cartridge connected to the blower box/mask portion. The connection of the hose to the hose portion may be co-axial with the annular structure and the grooved collar, thus enhancing the release of torque within the hose.

The fulcrum may have a counter torque that maintains the hook lever in a predetermined position, and the connector may include a magnet that attracts the hose portion to the blower box/mask portion by a force that is greater than the counter torque. In such an embodiment, bringing the hose portion and the blower box/mask portion in close proximity to each other places the hinged lever connector in the engaged state.

Also provided in various example embodiments is a nasal pillow system for treating sleep apnea that may include a nasal pillow. The pillow has a cavity wall that defines a cavity, and two nasal interface structures connected to and extending away from the cavity wall. The nasal interface structures are in fluid communication with the cavity through an internal air flow channel defined by the nasal interface structures. Each nasal interface structure includes a conical nasal interface with an opening to the airflow channel, a cylindrical trunk structure connected to the conical nasal interface and an annular relief pocket connected to the cylindrical trunk structure and to the cavity wall. The cross-sectional area of the internal channel across the connection between the cylindrical trunk structure and the conical nasal interface remains substantially constant. The connection between the annular relief pocket and the cavity wall defines substantially a plane, and a first portion of the annular relief pocket extends away from the plane while a second portion extends towards the plane. The connection between the cylindrical trunk structure and the conical nasal interface is adapted to maintain the cylindrical trunk structure substantially fixed relative to the conical nasal interface when the nasal pillow is used by a patient. The nasal pillow may be made of silicone and the cavity wall may vary in thickness.

The annular relief pocket may include an annular wall indentation extending into the cavity. The annular relief pocket is constructed so as to allow the opening to move towards and away from the plane and in a direction that is parallel to the plane. The annular relief pocket may define a cross-sectional area, and when the nasal interface structure moves, the area remains substantially constant.

The cavity wall may have a cartridge receiver opening, into which a removable valve cartridge may be disposed. A hose may be connected to the cartridge on one end and connected to a blower box on the other end, thus allowing therapeutic air pressure to be delivered to the patient. The pillow may also have a strap attachment structure, such as a hole or a tab, with which the pillow can be connected to a headgear assembly.

Also provided is a headgear assembly for use with a sleep apnea treatment mask that may include a first and a second asymmetric connectors on the mask. The assembly may also include a male strap with a complementary asymmetric connector adapted to mate with either the first or the second asymmetric connector in a single orientation, a surface that is in contact with the patient's head when the head gear assembly is installed, and a side wall substantially orthogonal to the surface that has a plurality of ratchet structures. The assembly may also have a female strap with a complementary asymmetric connector adapted to mate with either the first or the second asymmetric connector in a single orientation and a plurality of complementary ratchet structures constructed to mate with the ratchet structures, wherein the complementary ratchet structures extend substantially parallel to the patient's head.

The first and second asymmetric connectors may be a tab, and the male strap complementary asymmetric connector and the female strap complementary asymmetric connector may be a slot, or vice versa. A portion of the tab may have a wider groove, and another portion of the tab may have a narrower groove, and the slot may have a corresponding tongue edge with a portion that is thicker so as to mate with the wider groove portion of the tab and a tongue edge with another portion that is thinner so as to mate with the narrower groove portion of the tab. The first and second asymmetric connectors have an "L" shape.

The mask may include a nasal pillow.

The male strap may have a terminal end with a frictionless region, and the plurality of ratchet structures is proximally adjacent to the frictionless region. The female strap may have a terminal end and its plurality of complementary ratchet structures near the terminal end, and an opening proximally adjacent to the plurality of complementary ratchet structures. The opening is constructed to allow sufficient access to the frictionless region such that the patient can pull the male strap to mate the complementary ratchet structures with the ratchet structures.

Additional aspects, alternatives and variations as would be apparent to persons of skill in the art are also disclosed herein and are specifically contemplated as included as part of the invention. The invention is set forth only in the claims as allowed by the patent office in this or related applications, and the following summary descriptions of certain examples are not in any way to limit, define or otherwise establish the scope of legal protection.

4.0 BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure. It will be understood that certain components and details may not appear in the figures to assist in more clearly describing the invention.

FIG. 2C illustrates the hose portion of the hinged lever hose connector separated from the blower box/mask portion.

FIG. 2D illustrates a wedge-shaped hook engaging the grooved collar of the hinged lever hose connector.

FIG. 2E illustrates a wedge-shaped hook engaging a wedged-shaped grooved collar of the hinged lever hose connector.

FIG. 2F illustrates a hook engaging a wedged-shaped grooved collar of the hinged lever hose connector.

FIG. 10B is an enlarged view from FIG. 10A of the nasal interface structure.

FIG. 10C is an enlarged view from FIG. 10B of the annular relief pocket.

5.0 DETAILED DESCRIPTION OF EXAMPLE EMBODIMENTS

Figure 1:
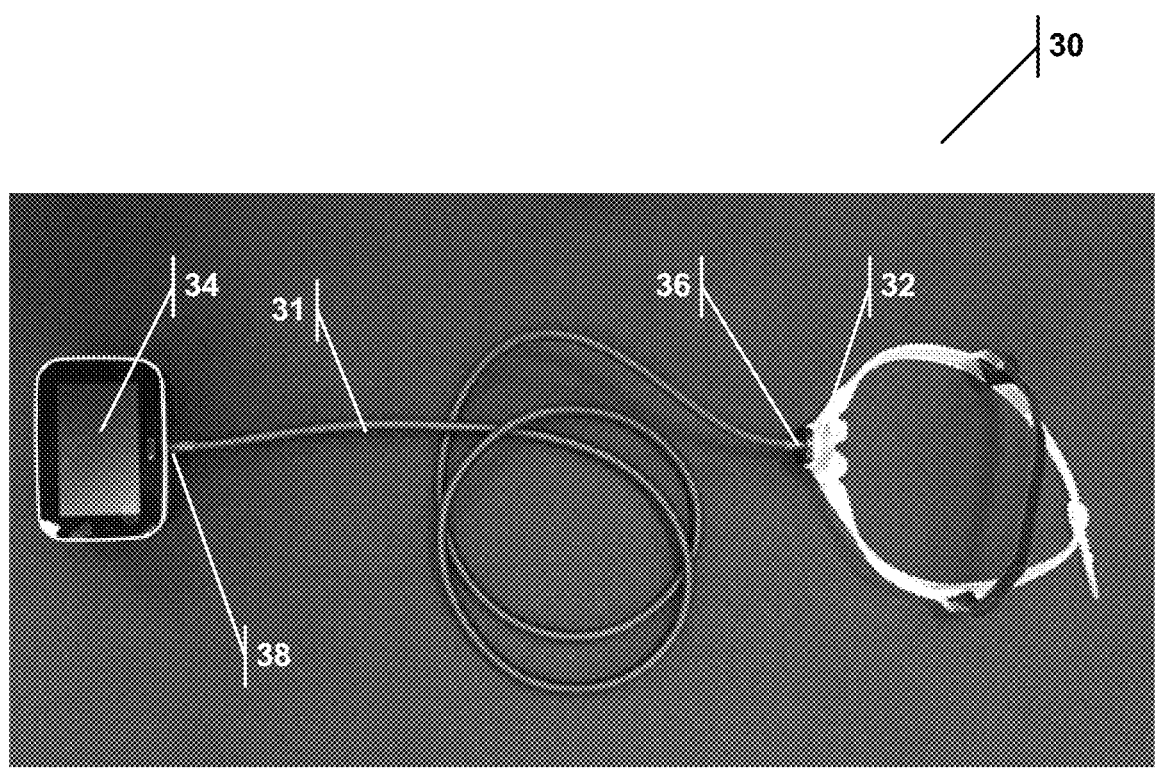
FIG. 1 illustrates a novel hose system to be used in the treatment of obstructive sleep apnea.

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, process operations well known to persons of skill in the art have not been described in detail in order not to obscure unnecessarily the present invention. Various techniques and mechanisms of the present invention will sometimes be described in singular form for clarity. However, it should be noted that some embodiments include multiple iterations of a technique or multiple mechanisms unless noted otherwise. Similarly, various steps of the methods shown and described herein are not necessarily performed in the order indicated, or performed at all in certain embodiments. Accordingly, some implementations of the methods discussed herein may include more or fewer steps than those shown or described. Further, the techniques and mechanisms of the present invention will sometimes describe a connection, relationship or communication between two or more entities. It should be noted that a connection or relationship between entities does not necessarily mean a direct, unimpeded connection, as a variety of other entities or processes may reside or occur between any two entities. Consequently, an indicated connection does not necessarily mean a direct, unimpeded connection unless otherwise noted.

The following list of example features corresponds with FIGS. 1-11B and is provided for ease of reference, where like reference numerals designate corresponding features throughout the specification and figures:

Hose System (Prior Art) 10
Hose (Prior Art) 15
Mask (Prior Art) 20
Rotational Hose Fitting (Prior Art) 22
Blower Box (Prior Art) 23
Mask Hose Fitting (Prior Art)24
Elbow (Prior Art) 25
Elbow Sweep (Prior Art) 26
Elbow Outlet (Prior Art) 27
Elbow Outlet Rotation (Prior Art) 28
Hose Torque Rotation (Prior Art) 29
Hose System 30
Hose 31
Mask 32
Blower Box 34
Rotatable Mask Connector 36
Rotatable Blower Box Connector 38
Hinged Lever Hose Connector 39
Hose Portion 40
Blower Box/Mask Portion 42
Annular Structure 43
Fulcrum 44
Hook Lever 45
Disengagement Surface 50
Hook Release Pressure Position 51
Hook Release Movement 52
Grooved Collar 55
Connection Housing 56
Hook 60
Magnet 65
Complementary Magnetic Structure 70
Rotational Freedom of Hinge Connector 75
Translations engagement/disengagement movement of connector 80
Mask Assembly 100
Nasal Pillow 105
Removable Valve Cartridge 110
Head Gear Assembly 115
Male Strap 120
Female Strap 125
Male Strap Ratchet Structure 130
Female Strap Complementary Ratchet Structure 135
Back Strap Connection Hole 140
Back Strap 141
Indentations 145
Protrusions 150
Strap Surface 151
Strap Side Wall 152
Strap Frictionless Region 155
Female Strap Housing 160
Opening 165
Asymmetric Friction Fit Locking Tab 170a, 170b
Asymmetric Friction Fit Locking Slots (170c, 170d)
Wider Tab Groove 171
Narrower Tab Groove 172
Thick Strap Tongue Edge 173
Thinner Strap Tongue Edge 174
Nasal Interface Structures 175
Internal Air Flow Channel 176
Cartridge Receiver Opening 180
Annular Relief Pocket 185
Cylindrical Trunk Structure 190
Conical Nasal Interface 195
Conical Nasal Interface Opening 197
Sealing Surface 200
Annular Relief Pocket Wall 202
Nasal Pillow Cavity 205
Cavity Wall 210
Cavity Wall Plane 215
Cross-sectional Area Defined by the Annular Relief Pocket 220

5.1 Dual Rotatable Hose and Connector for Use with CPAP Treatment Systems

The applicant intends to overcome the shortcomings of conventional CPAP by developing a low flow rate CPAP device that requires flow rates ~10× lower (10-45 L/min) to maintain pressure between 4-20 CM-H2O in order to "splint" the airway. These devices are disclosed in the aforementioned patent applications. As a result, the hose necessary for this reduced flow rate has a diameter of less than 10 mm as compared to the 22 mm traditional hose. The new hose system is comprised of three main components: the hose, mask connector, and blower box connector.

The new hose is a composite silicon-coated braided tube that is lightweight, has excellent flexibility, good flow rates, strong crush resistance, and high durability, and is described in U.S. patent application Ser. Nos. 15/334,243 and 62/246,477, both of which are incorporated herein by reference. The new mask connector is a piece that can detach and attach to the mask while being rotatable and allowing directionality of the hose as it exits the mask. Lastly, the new blower box connector may also use a rotatable magnet to connect to the air-pressurizing device for easy and quick connections and disconnection.

Figure 12A:
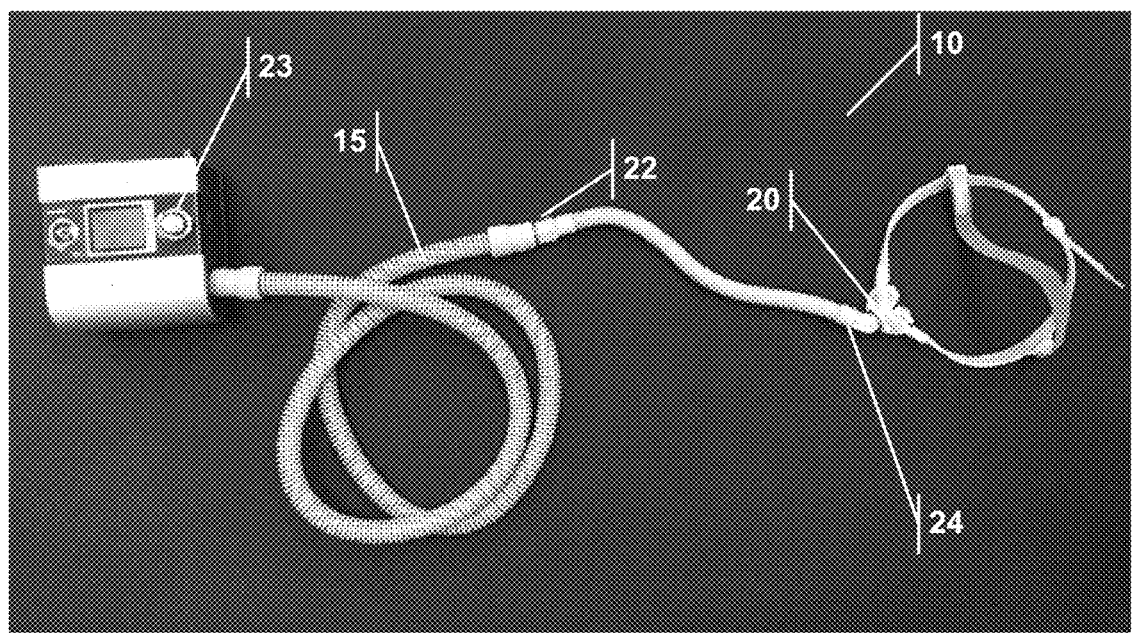
FIG. 12A illustrates the prior art hose system.

As shown in FIG. 12A, in traditional prior hoses systems 10, the hose 15 either only rotates at the mask 20 or at the end of the 2 ft mid connector 25. However, since the blower box 26 does not rotate, this can lead to configurations where the long 4-6 ft portion of the hose ends up building up torque tension, resulting in coiling of the hose 15. The problem with coiling is that it can lead to kinks, decreased flexibility, decreased range of motion, and shorter length of the hose. These factors can lead to patient issues such as pulling the CPAP blower off the night stand, dislodging the mask from the patient's face, and limiting airflow resulting in the patient not receiving therapy as intended.

Figure 12B:
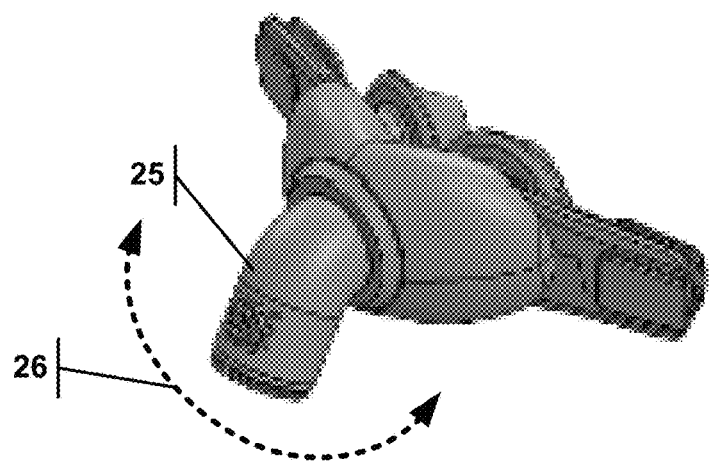
FIG. 12B illustrates the prior art elbow that connects the mask to the hose.
Figure 12C:
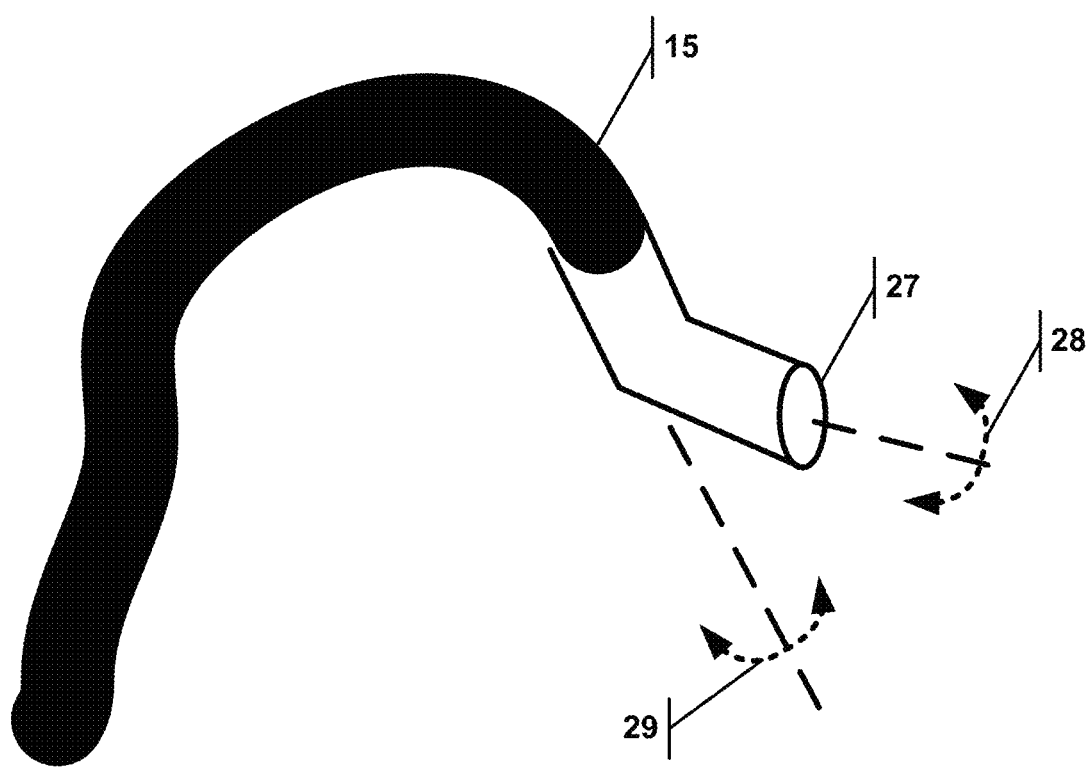
FIG. 12C illustrates the prior art torqueing of the hose relative to the elbow outlet.

Moreover, in conventional CPAP masks, the mask hose fitting 24 has a vent on the outer surface and is bent like an elbow. The elbow 25 can rotate in a wide sweep 26, as shown in FIG. 12B. A significant drawback to this elbow design is that any built-up torque in the hose can only be released when the elbow has the room to make its sweep 26. Further, the built-up rotational torque in the hose 29 is not co-axial with the elbow outlet (27, 28), which is connected to the nasal pillow, as shown in FIG. 12C. Thus, the hose rotational torque 29, even if there is room for the elbow 25 to make the sweep 26, is not aligned with the elbow outlet rotation 28, and will not efficiently unwind.

In the prior mask connector design, the hole size is around 15 mm in diameter to order to allow for large amounts of air flow to enter the mask. Also, this mask connector attaches via a rubber press fit or snap fit, to ensure that the hose is secure to the mask and does not leak air. However, this connector is problematic because it can be difficult to connect and disconnect the hose for maintenance and storage.

The new hose system 30, shown in FIG. 1, is comprised of three main components: the hose 31, mask connector 36, and blower box connector 38. It is novel because it has a rotatable mask connector 36 and rotatable blower box connector 38. Dual rotation helps, as every area along the hose 31 has the ability to rotate in order to decouple torque tension, thus mitigating the coiling issue.

Figure 2A:
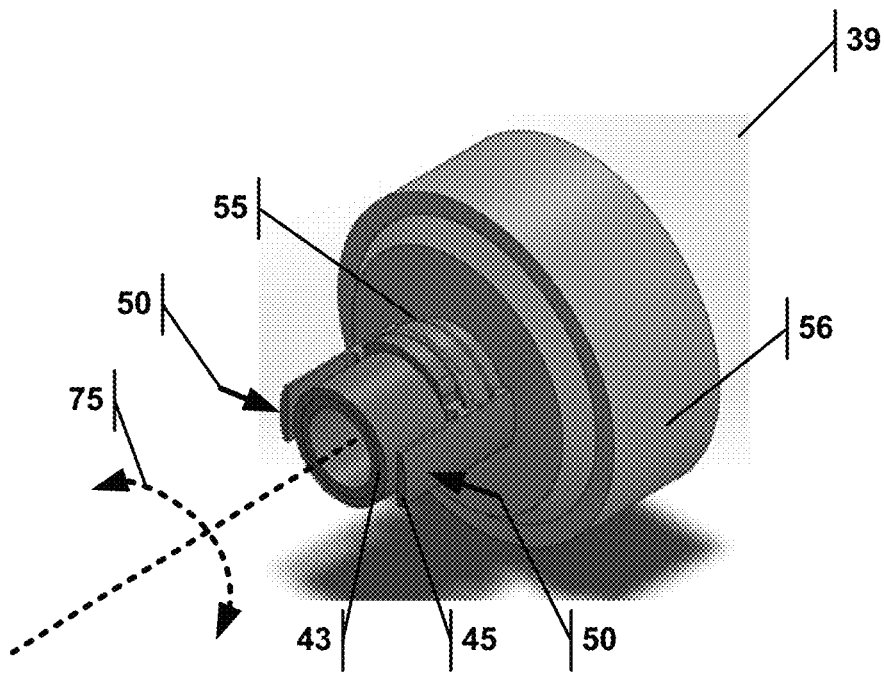
FIG. 2A is an isometric view of a hinged lever hose connector in the engaged state.
Figure 2B:
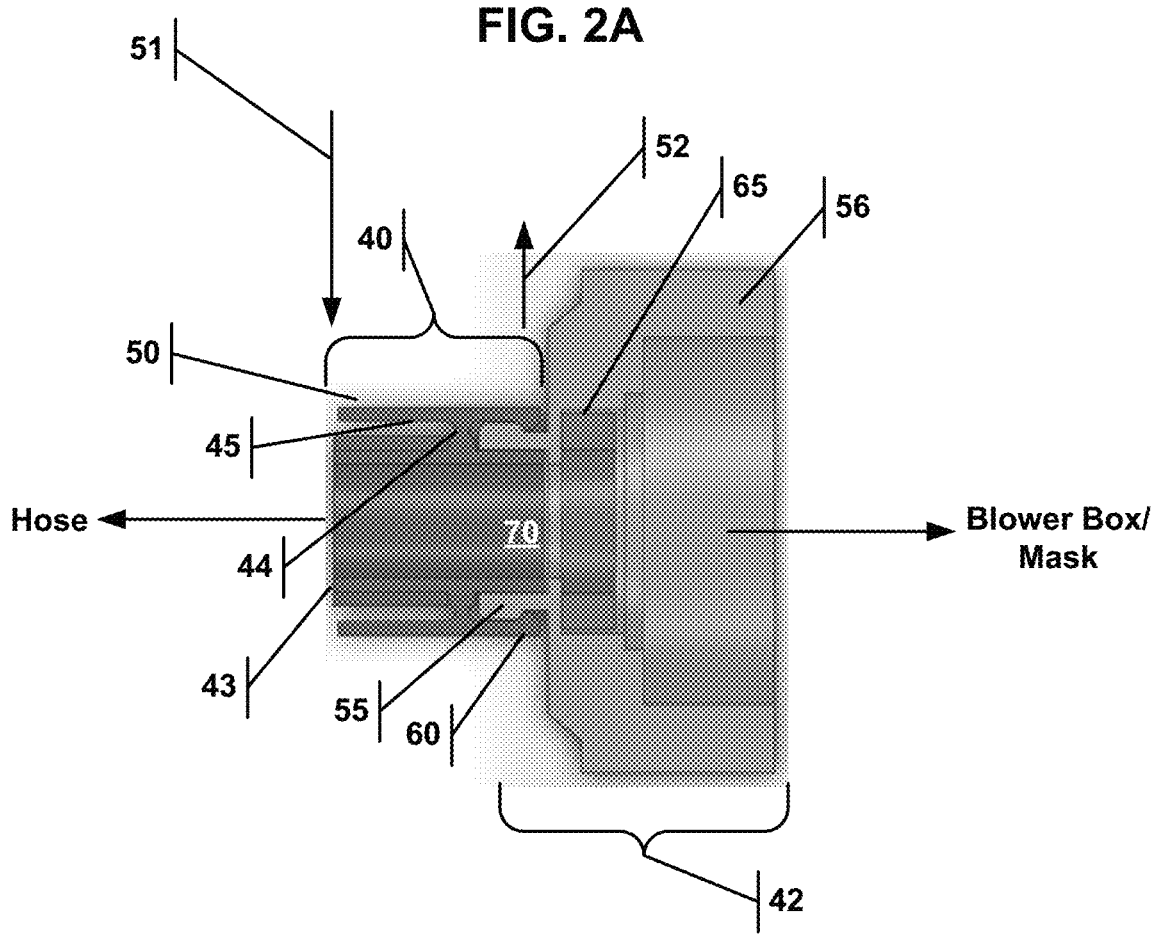
FIG. 2B is a cross-sectional view of the hinged lever hose connector.

Shown in FIGS. 2A and 2B is a unique hinged lever hose connector 39 that is rotatable along the same axis in which the hose connects to the connector; thus, the hose rotational torque can more efficiently unwind about the rotatable hinged lever hose connector 39. This connector design can be used as both the rotatable mask connector 36 and the rotatable blower box connector 38 shown in FIG. 1. It should be noted that the term mask is used throughout this disclosure; however the mask may be simply a nasal pillow as opposed to a mask structure that covers both the patient's mouth and nose. Thus, the connector 39 described below may also be used in conjunction with nasal pillows.

The connector 39 is made up of two portions: the hose portion 40 and the blower box/mask portion 42. The hose portion has an annular structure 43 that is connected to a hook lever 45 via a fulcrum 44. The hook lever 45 may rotate about the fulcrum 44. At the end of the hook lever 45 is a hook 60 that mates into a grooved collar 55 found on the blower box/mask portion 42, thus securing the hose portion 40 of the connector to the blower box/mask portion 42. The grooved collar 55 is connected to the connection housing 56, which is then connected to the blower box, mask, nasal pillow or valve cartridge.

By pressing the hook lever 45 at the hook release pressure position 51, the hook releases, as shown by movement arrow 52; thus, the hose portion 40 of the connector can be detached from the blower box/mask portion 42, as shown in FIG. 2C. In operation, the patient would pinch both hook levers at the disengagement surface 50 to release the hose connector 39.

The hook 60 can be wedged-shaped such that as it is pressed against the grooved collar, the translational movement 80 of the hose portion relative to the blower box/mask portion causes the hook lever 45 to hinge about the fulcrum 44, as shown in FIG. 2D. To achieve a similar result, the edge of the grooved collar can also be wedge-shaped as shown in FIGS. 2E and 2F. The fulcrum 44 preferably has some counter torque, such that when the hook 60 moves in the hook release direction 52, the counter torque will bring the hook back to its original position when the patient stops placing pressure at the disengagement surface 50.

The hook 60 can travel along the grooved collar 55, thus allowing for rotational freedom as, shown by arrow 75 of the hose portion 40 relative to the blower box/mask portion 42. Indeed, the grooved collar 55 may also rotate relative to the connection housing 56 of the blower box/mask portion, further enhancing the rotational movement of the hose. Additionally, a magnet 65, along with a complementary magnetic structure 70, may be used to allow the connector 39 to self-connect, with the magnetic attraction force being sufficient to pull both portions together and to overcome the counter torque of the fulcrum.

As is clear from FIGS. 2A-2C, the connector 39 has two states: an engaged state where the hook 60 is disposed of in the groove of the grooved collar 55, thereby connecting the hose portion 40 to the blower box/mask portion 42; and a disengaged state where the hook lever 45 is rotated about the fulcrum 44, thereby moving the hook 60 away from the groove, allowing the hose portion 40 to be disconnected from the blower box/mask portion 42.

Having a locking/unlocking mechanism is advantageous in that there is no need to balance disconnection force with patient ease of disconnecting. Designs with a locking/unlocking mechanism can easily be attached/detached by activating the mechanism but cannot be removed if the mechanism is not activated. This reduces the risk that the hose may accidently disconnect during sleeping.

5.2 Head Gear for Use with CPAP Treatment Systems

Figure 3:
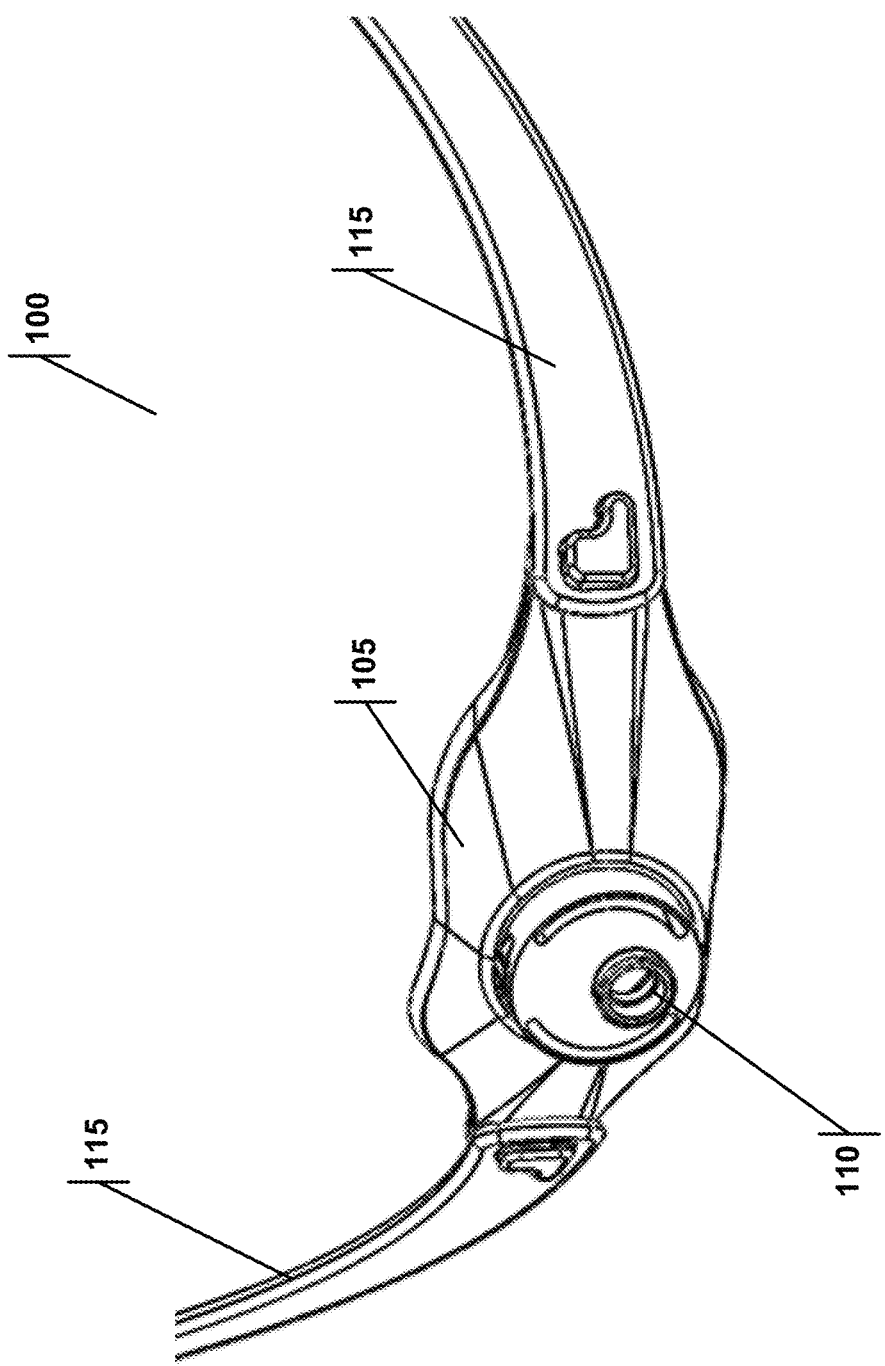
FIG. 3 illustrates a novel mask assembly.

FIG. 3 shows an embodiment of a mask assembly 100 to deliver pressurized air to nasal passages of a patient's nose. The mask assembly 100 includes a removable valve cartridge 110, a nasal pillow 105 and a removably attached headgear assembly 115. The headgear assembly 115 may be comprised of two straps (male and female) and a hook and loop fastening back strap, discussed in more detail below.

The headgear assembly 115 is used to stabilize the nasal pillow 105 so as to retain sealing forces upon the nose. The nasal pillow 105 and each silicone strap may be made of 20-60 shore(A) silicone, preferably using 35-45 shore(A). The nasal pillow 105 and headgear assembly straps are also textured to reduce the 'stickiness' or 'tackiness' of the silicone. This texturing could either be a small to large grit bead blast, or it could be a micro-texturing, MT-11001-11007.

Figure 4A:
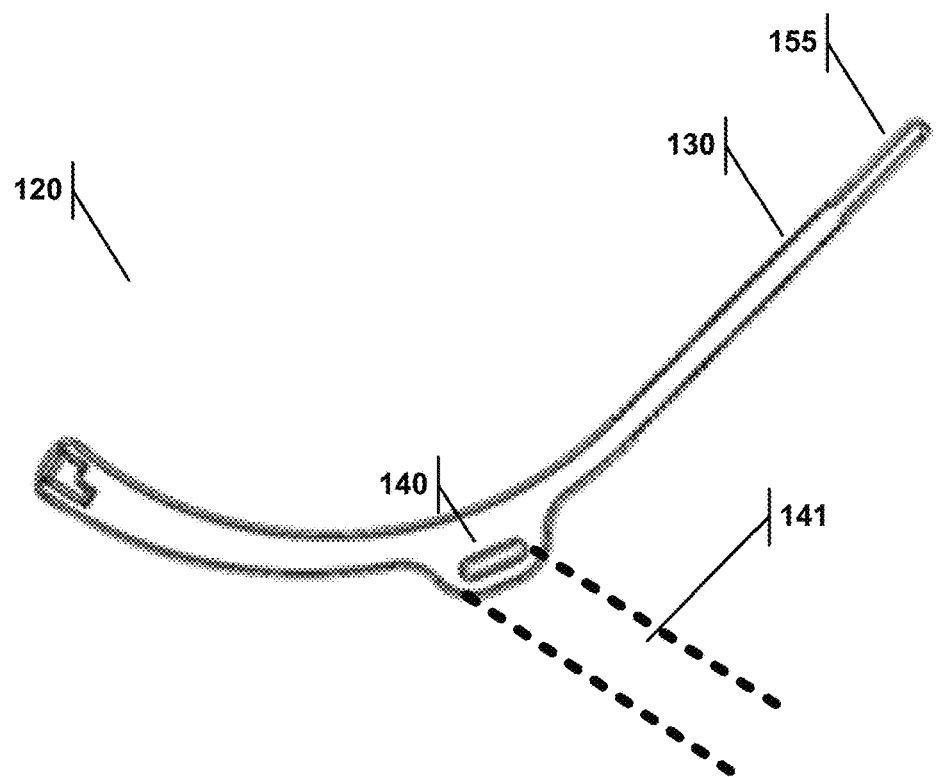
FIG. 4A illustrates a male strap of the headgear assembly.
Figure 4B:
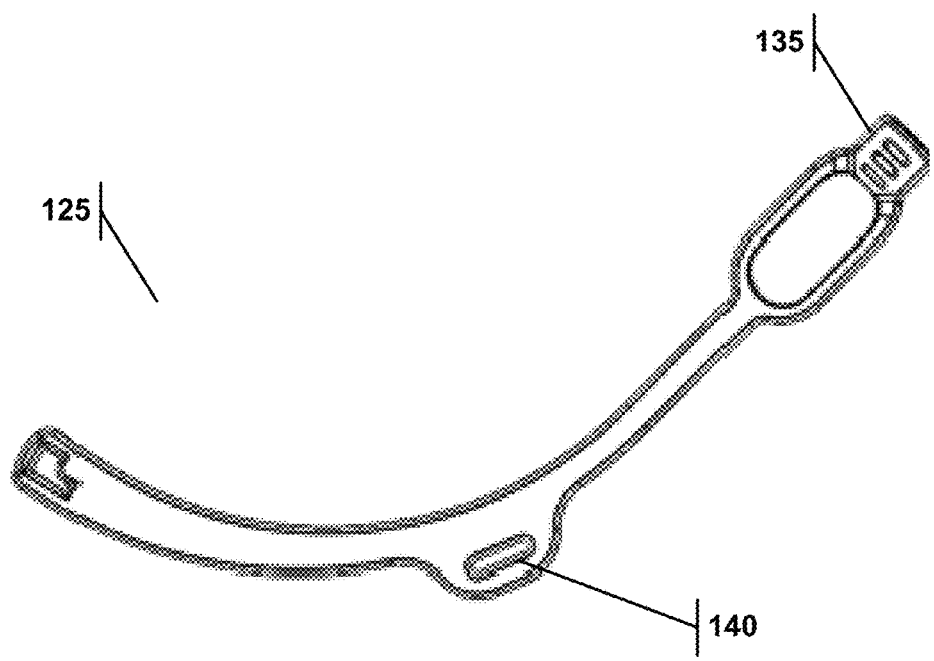
FIG. 4B illustrates a female strap of the headgear assembly.
Figure 5A:
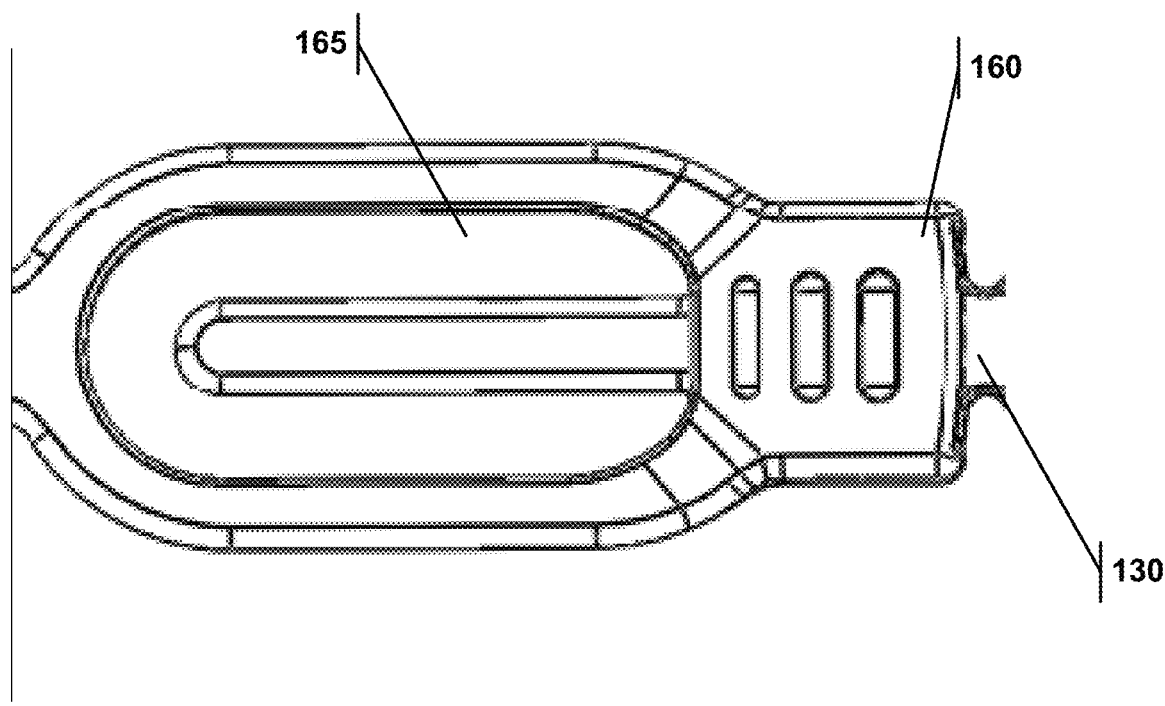
FIG. 5A shows a top view of the ratchet mechanism of the headgear assembly.
Figure 5B:
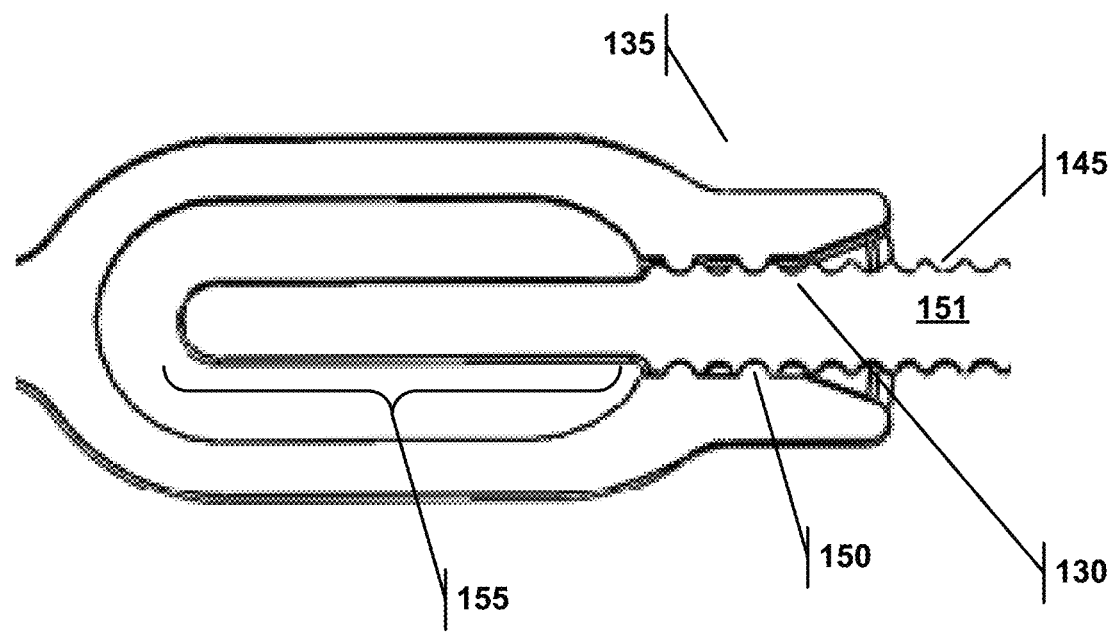
FIG. 5B shows a cross-sectional view of the ratchet mechanism of the headgear assembly.
Figure 6A:
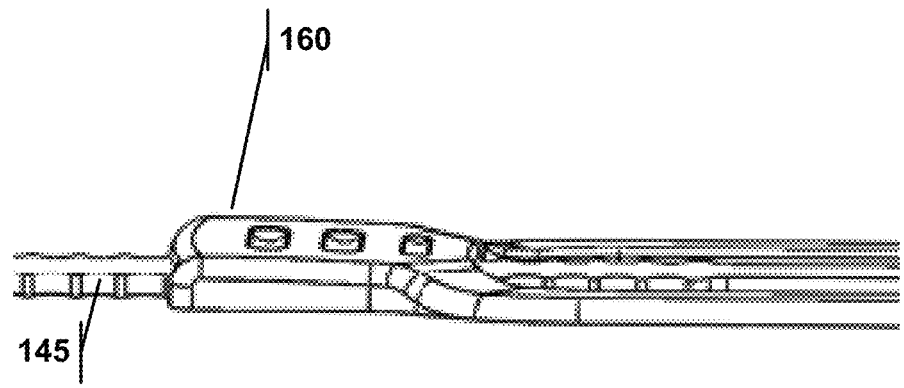
FIG. 6A shows a top cross-sectional isometric view of the ratchet mechanism of the headgear assembly.
Figure 6B:
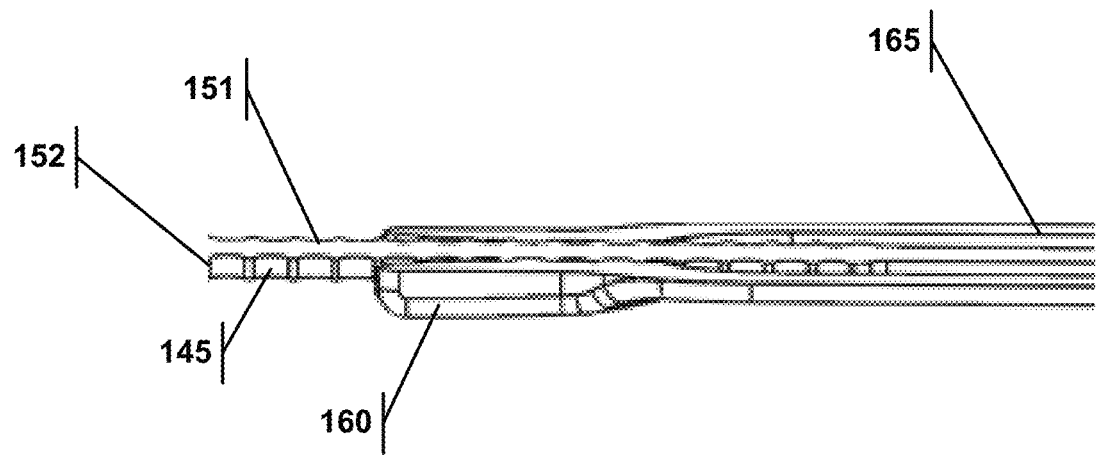
FIG. 6B shows a bottom cross-sectional isometric view of the ratchet mechanism of the headgear assembly.

The straps of the headgear assembly 115 are made up a male strap 120 and a female strap 125, as shown in FIG. 4A and FIG. 4B, respectively. These straps are configured to pass over the left and right cheeks of the patient, between the eye and the ear, and meet on top of the patient's head. The straps lock together utilizing a friction based bidirectional ratcheting mechanism shown in FIGS. 5A and 5B, with a male strap ratchet structure 130 fitting into a female strap complementary ratchet structure 135. These ratchet structures allow for the adjustment of the strap assembly to accommodate various head sizes. FIG. 5B is a cross-sectional view intended to show the operation of the ratchet structures.

Along the length of both the male and female straps lies an oblong back strap connection hole 140 (see FIGS. 4A and 4B) that allows for the passing through of a self-adherent back strap 141 that connects with itself, thus uniting the male and female straps around the back of the patient's head. The back strap may use a soft hook and loop fastener to self-connect, and this connection can be adjusted to ensure the correct fit for the patient. Since the hook and loop fastener do not readily adhere to hair, adjustment of the back strap would not tug on at the patient's hair.

Turning back to FIGS. 5A and 5B, the male strap ratchet structure 130 uses a linear series of indentations 145 running along the length of the main body of the male strap 120. These indentations 145 are configured to interlock with one or more corresponding sets of protrusions 150 in the housing of the female strap 125. The depth and corresponding height of these indentations and protrusions is preferably between 0.025 in and 0.1 in. In another embodiment, the protrusions are running along the length of the male strap and the indentations are in the housing of the female strap. While the protrusions and indentations are shown in FIGS. 5A and 5B as cylindrical, it would be apparent to one of skill in the art that the shapes can vary. A non-limiting example may be spherical or rectilinear.

When the headgear assembly 115 is installed on a patient, the straps 120 and 125 have a flat surface 151 that lays on the surface of the patient's head. Substantially orthogonal to this surface is the side wall 152 of the strap, and it is on this wall that the indentations 145 are disposed on the male strap 120 (see FIG. 6B). The female strap 125 also has a flat surface that lays on the surface of the patient's head, and the protrusions 150 extend substantially parallel to this surface. The benefit of this design is that the ratchet structures engage each other parallel to the surface defined by the patient's head, such that the male strap can engage and lock with the female strap regardless of what side the female and male straps are connected relative to the nasal pillow. Moreover, having the ratchet structures parallel to the surface defined by the patient's head, means that regardless of how the straps are connected to each other, the patient will not experience discomfort from a ratchet structure that extends from the surface 151 into the patient's head. This is a significant shortcoming in previous designs.

The friction caused by the interlocking of the straps is great enough to ensure that the straps remain interlocked through normal use but can be easily pulled through the housing to adjust the total size of the headgear assembly during fitting. The linear force required to open the headgear should be between 0.5-2 lbs. The male strap 120 is configured with a frictionless region 155 near the end of the strap that is terminal from the connection to the mask. This terminal end therefore has the frictionless region 155, and the ratchet structure 145 is proximally adjacent to this region, meaning that the ratchet structure is closer (more proximate) to the mask connection end of the strap. This frictionless region 155 can be inserted into the female strap housing 160 freely and without friction as seen in FIGS. 5A and 5B. The female strap 125 may also have an opening 165 proximally adjacent to the female strap complementary ratchet structure 135, which allows the patient to grab the end of the male strap 120 as it emerges from the female strap housing 160. Preferably, this frictionless region 155 should be long enough to enter between 25-75% of the opening before encountering resistance from the protrusions, as seen in FIG. 5B. In a preferred embodiment, this should be more than ¾ inch. This allows the patient to easily insert the male strap 120 and grab hold of the male strap 120 after it passes through the female strap housing 160. Once the patient has taken hold of the male strap 120, the patient can easily exert more force upon the male strap 120 to adjust its overall length to fit their head size.

A common problem with headgear assemblies is that they are often complicated and can be easily assembled in an incorrect way. This problem is coupled with inherent situation that headgear assemblies may need to be assembled in a low-light environment or even in the dark. The nasal pillow 105 and headgear assembly 115 presented herein are designed to be extremely easy to assemble, or, more accurately, very difficult to assemble incorrectly. The new design is free from a left-right orientation and forces the patient to assemble the headgear in a correct up-down orientation.

This vertical symmetry allows for the interchanging of the male or female strap (120, 125) to be used on the left or right side of the nasal pillow 105. A patient could attach the male strap 120 to the left side of the pillow 105 or the right and either way the assembly would be functional. Regardless of how the male and female straps are connected to the mask, they can mate and lock with each other as shown in FIGS. 5A-6B. This design ensures that the patient cannot incorrectly assemble the headgear straps (120, 125) in relation to the pillow 105 with regards to the left or right orientation. It also allows for the patient to swap the male or female strap (120, 125) from one side to the other depending on a personal preference.

Figure 7A:
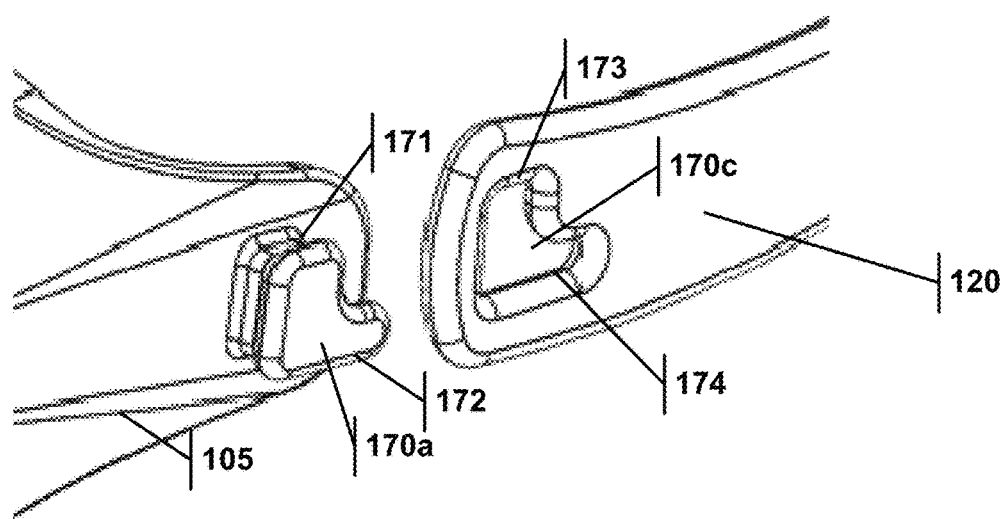
FIG. 7A illustrates the connection between the nasal pillow and the headgear assembly.
Figure 7B:
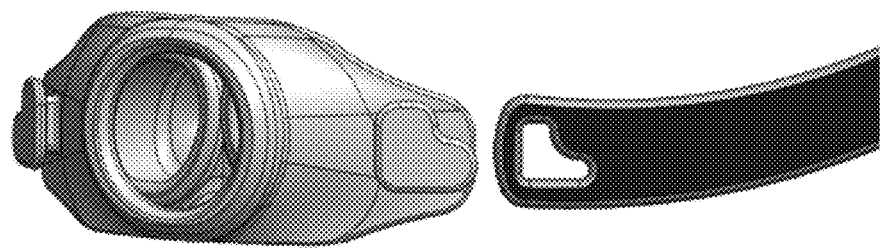
FIG. 7B illustrates the proper orientation of the strap to make a connection with the nasal pillow.
Figure 7C:
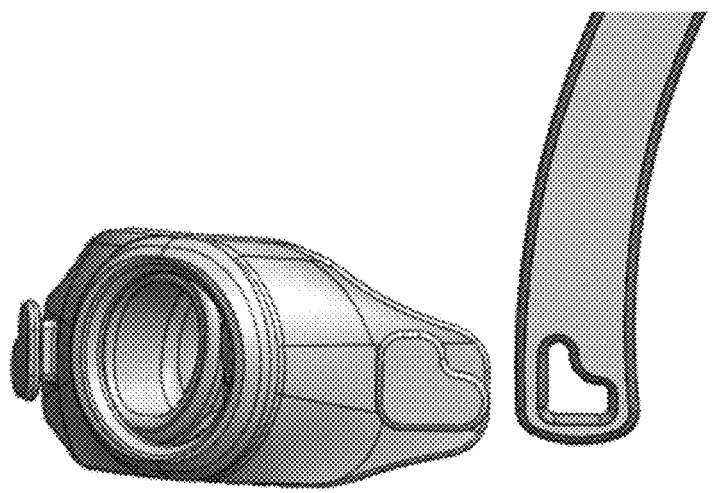
FIG. 7C illustrates an improper orientation of the strap to make a connection with the nasal pillow.
Figure 8:
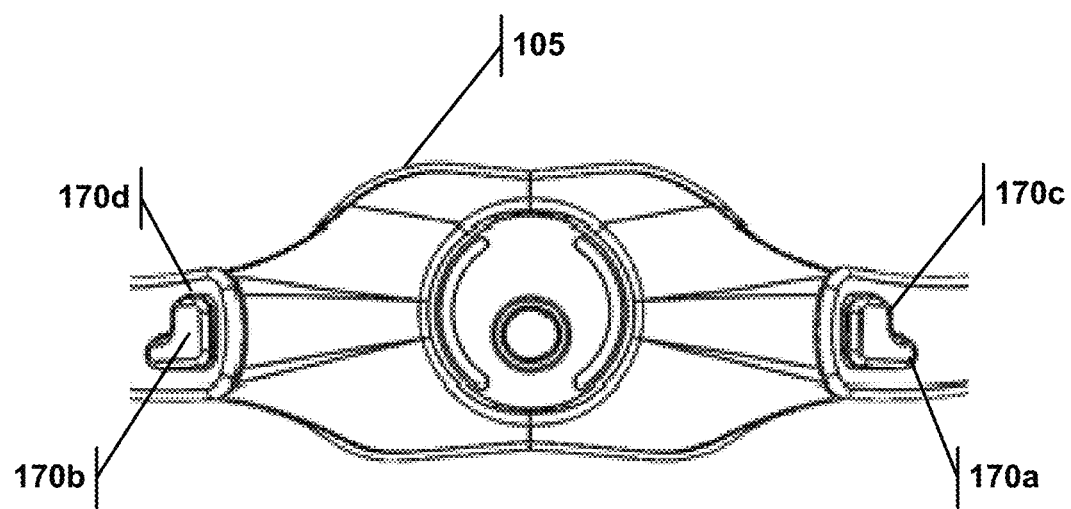
FIG. 8 illustrates the connection between the nasal pillow and the headgear assembly.

Additionally, the design addresses the other cause of incorrect assembly of the pillow to the headgear, the failure to correctly position the orientations of the straps. To address this problem, the design features a pair of asymmetric friction fit locking tabs 170a and 170b, as shown in FIGS. 7A-8. These tabs are aligned horizontally across the nasal pillow 105, as shown in FIG. 8. The combination of the asymmetric friction fit locking tabs (170a, 170b) with their horizontal alignment creates a design that cannot be assembled incorrectly without the use of excessive force and omission of obvious visual cues that indicate that it is assembled incorrectly. The asymmetric friction fit locking tab (170a, 170b) are configured generally in the shape of an 'L'. This ensures the patient will fit the L-shaped tab into the L-shaped hole on the strap. To further ensure proper orientation of the strap to the nasal pillow, one groove of the tab 170a may be wider (171) than the other (172), with a corresponding asymmetric friction fit locking slots (170c, 170d) on the straps with a thicker (173) and thinner (174) tongue edges. The combination of the asymmetric L-shape and the thicker/thinner edges, creates a structural interference that informs the patient that the strap is properly (FIG. 7B) or improperly (FIG. 7C) attached to the tab. While the asymmetric tab design or the thinner/thicker edge design alone would give this information to the patient, using both features in advantageous because the strap 120 and the nasal pillow 105 may be constructed of an elastomeric material that can be stretched. So, for example, in FIG. 7C the strap could be mounted to the nasal pillow by stretching the material. But having both the L-shaped and the thinner/thicker orientation features would create more structural interferences that would encourage the patient to re-orient the strap relative to the nasal pillow.

Figure 9A:
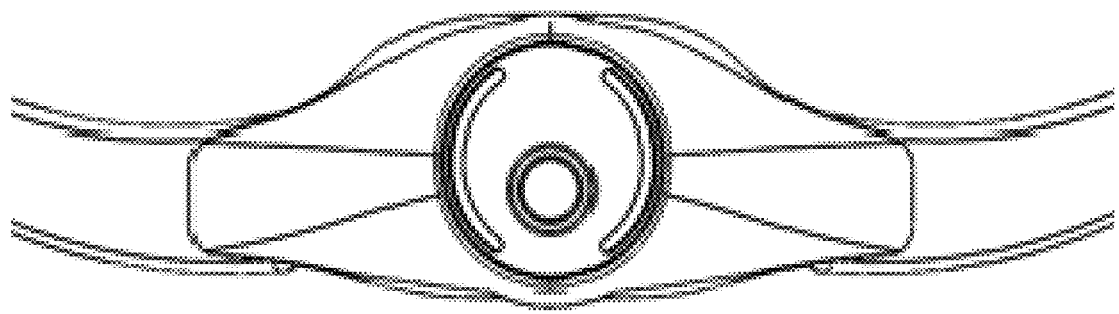
FIG. 9A is a front view of the nasal pillow with a valve cartridge connected to the headgear assembly.
Figure 9B:
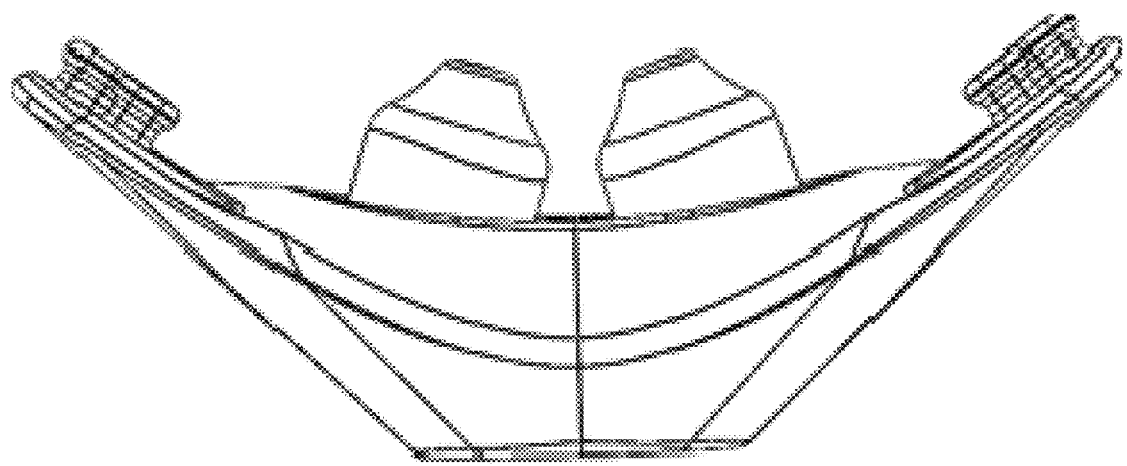
FIG. 9B is a top view of the nasal pillow showing the headgear connection structures (asymmetric friction fit locking tabs).

The asymmetric friction fit locking tabs (170a, 170b) functionally lock each strap to the nasal pillow 105 with sufficient strength to remain locked through normal use, but they can be easily be assembled or disassembled. Whereas the asymmetric friction fit locking tabs (170a, 170b) are shown in FIG. 7A-8 as being placed on the outside surface of the nasal pillow 105 (i.e., the surface facing away from the patient), the tabs can also be mounted on the inside surface of the nasal pillow (i.e., the surface facing towards the patient), as shown in FIGS. 9A and 9B. Alternatively, the straps (120, 125) may have the asymmetric friction fit locking tabs (170a, 170b) while the nasal pillow 105 has the corresponding L-shaped slot. In short, the asymmetric friction fit locking tabs (170a, 170b) and the asymmetric friction fit locking slot (170c, 170d) are the connection between the straps and the mask, and should be complementary to each other.

While prior strap designs use asymmetric features or keys to ensure a specific left/right, and up/down orientations, this embodiment uses simple design features to ensure there is no left/right orientation and that is has to be forcefully assembled incorrectly and with visual ques to show the incorrect mating of parts with regard to the up/down and left/right orientations.

5.3 Nasal Pillow for Use with CPAP Treatment Systems

Figure 10A:
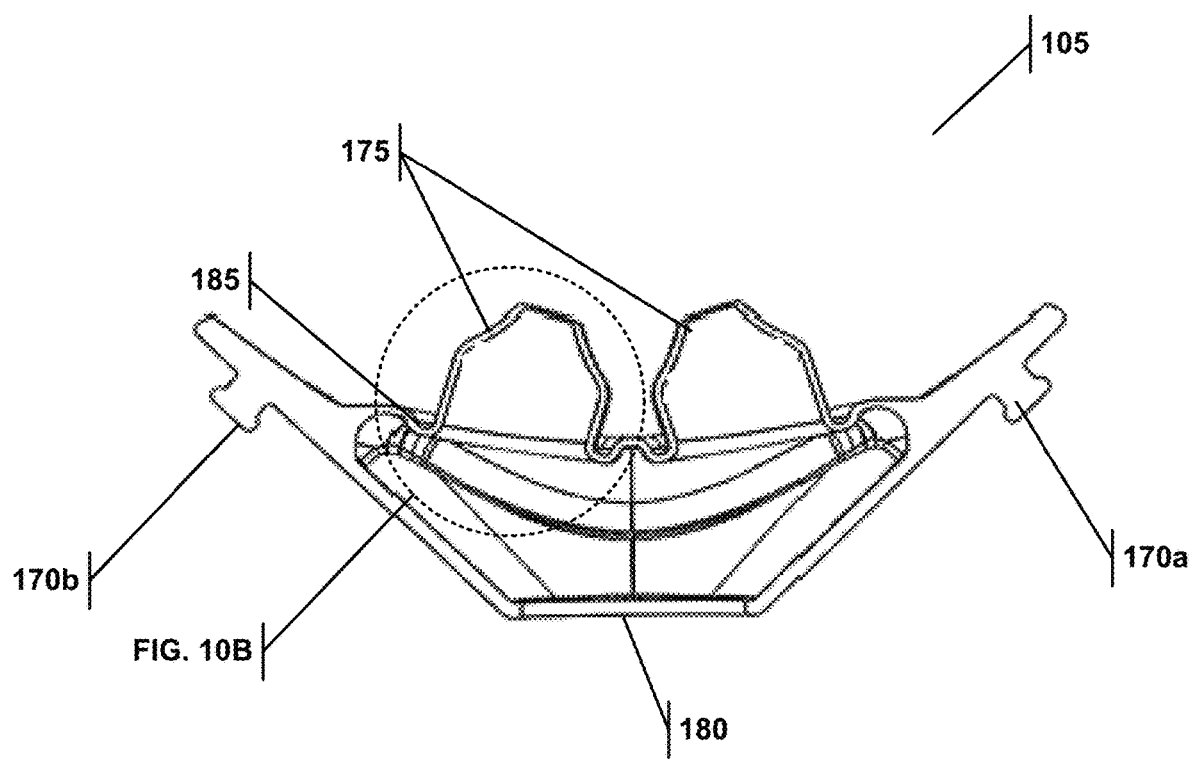
FIG. 10A is a cross-sectional view of the nasal pillow, illustrating the nasal interface structures.

As shown in FIGS. 10A, 10B and 10C, the nasal pillow is a structure, preferably of silicone, defining a cavity with a pair of lateral connector tabs (i.e., asymmetric friction fit locking tabs (170a, 170b)) disposed on each sides of the pillow. The nasal pillow 105 has two sides: a first side which includes a pair of nasal interface structures 175 and the second having a cartridge receiver opening 180 configured to accept an insertable and removable valve cartridge. The insertable valve cartridge is described in U.S. Patent Applications 62/532,240, 62/465,905, and Ser. No. 14/930,284, incorporated herein by reference. The size of cartridge receiver opening 180 must fit tight enough around the valve cartridge so that it does not move or disassemble through use but must be able to be easily disassembled for cleaning. It should be noted that the hinged lever hose connector described above may be used with the valve cartridge. As a non-limiting example, the blower box/mask portion 42 may be connected to or integrated with the valve cartridge.

The nasal interfaces 175 are integrally connected to the main pillow body via an annular relief pocket 185. The nasal interfaces 175 have an internal air flow channel 176 in fluid communication with the cavity 205 on one end and the opening 197 on the other end. Each nasal interface 175 is generally an oblong cylindrical trunk structure 190 integrally connected to an oblong conical nasal interface 195 to match the general nasal geometry. Conical interface may have a slight concavity and is in configured to be partially inserted into the nasal pathway in order to create a sealing surface 200 on underside of the patient's nose. The oblong conical nasal interface 195 is connected to the oblong cylindrical trunk structure 190 without a flare out structure such that the air flow path is not disturbed as it travels from the nasal pillow cavity 205 to the opening 197. This smooth airflow path enhances patient comfort and reduces noise.

Some prior art designs have nares insertion structure that flares out before connecting to the tube extending from the cavity, resulting in a mushroom shape. This construction, however, allows for significant movement of the nares insertion structure relative to the tube extending from the cavity, and as these two structures move relative to each other, the air flow path becomes more tortured and noisy, and less comfortable for the patient.

The present design has a continuous connection between the oblong conical nasal interface 195 and the oblong cylindrical trunk structure 190 (without a flare out structure), providing more support to the conical nasal interface 195 and reducing the movement of the conical nasal interface 195 relative to the cylindrical trunk structure 190; thus, the system maintains a more constant and comfortable air flow path. In other words, the cross-sectional area of the internal air flow 176 channel remains substantially constant across this connection and does not increase. Also, the connection between the cylindrical trunk structure 190 and the conical nasal interface 195 maintains the cylindrical trunk structure 190 substantially fixed relative to the conical nasal interface 195 when the nasal pillow is used by a patient.

The edge of the conical nasal interface 195 merges into the cylindrical trunk structure 190 and extends into the annular relief pocket 185, allowing for the maximum airflow to be delivered to/from the patient without any unnecessary restrictions. The annular relief pocket 185 is an annular wall indentation extending into the main cavity 205 of the nasal pillow. This annular wall indentation creates a 'well' or a 'moat' like structure around the nasal interface structure. The wall of the annular relief pocket wall 202 curves into the nasal pillow cavity 205 and then curves away from the cavity 205, connecting to the cavity wall 210.

Figure 11A:
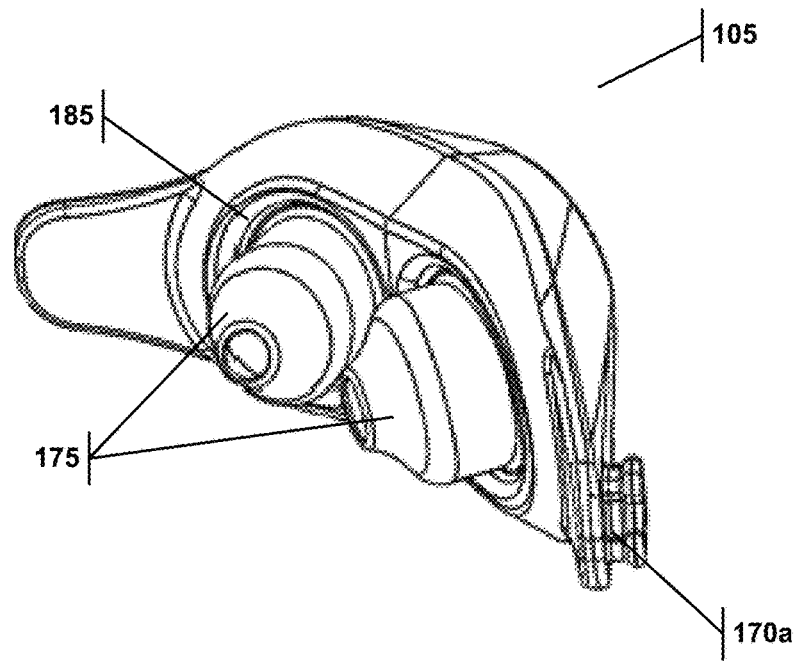
FIG. 11A is a side isometric view of the nasal pillow, illustrating the nasal interface structures and annular relief pockets.
Figure 11B:
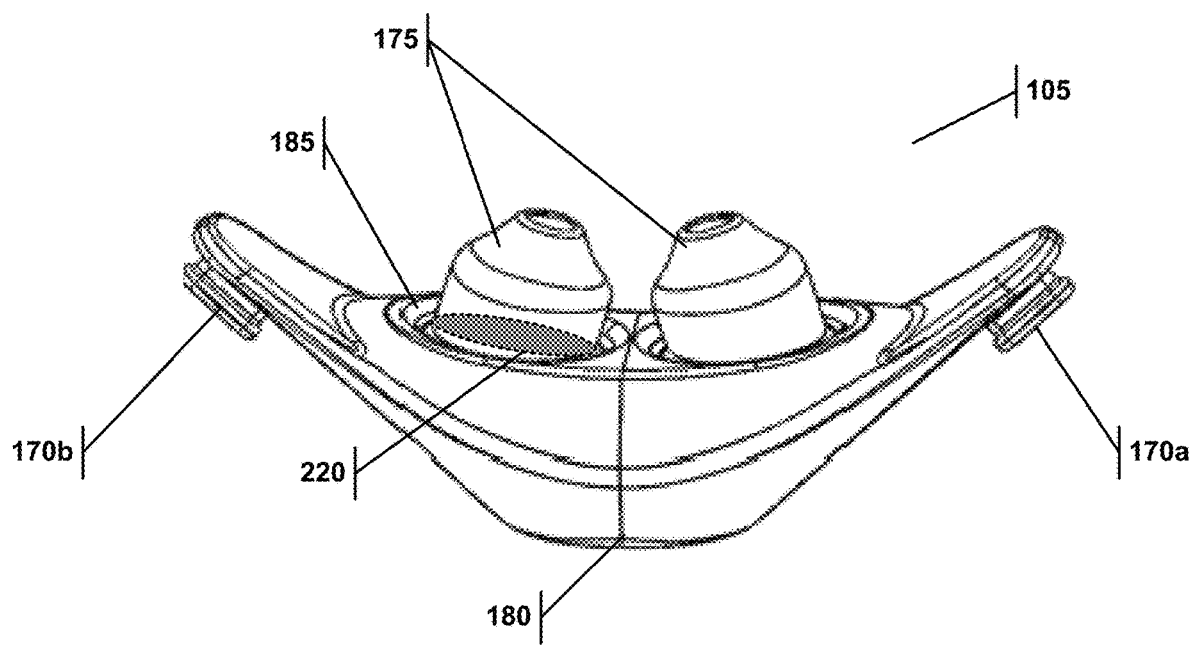
FIG. 11B is a side isometric view of the nasal pillow, illustrating the nasal interface structures and annular relief pockets.

This is shown in greater detail in FIG. 10C. The cavity wall 210 connection to the annular relief pocket defines a plane 215 (or substantially a plane), and the portion of the annular relief pocket wall 202a that is connected to the cavity wall 210 extends away from this plane 215 into the cavity 205, and a second portion 202b curves back and extends towards the plane 215 to meet the cylindrical trunk structure 190. The function of the annular relief pocket 185 is to provide articulation of the opening of the nasal conical interface 197 in the x, y and z directions (relative to plane 215) without creating an unnecessary flow restriction and while maintaining a nasal seal. When the opening 197 moves, the cross-sectional area defined by the annular relief pocket (shown as shaded oval 220, FIG. 11B) remains substantially constant such that the delivery of air flow to the patient is not restricted. Isometric views of the nasal pillow 105, the nasal interfaces structures 175 and annular relief pockets 185 are shown in FIGS. 11A and 11B.

There may be differently sized nasal pillows, each having a different nasal interface geometry to accommodate a variety of patients. Each size may be configured with an annular relief pocket to extend around the nasal interfaces. While the nasal interface structure geometry may change, the opposite side of the nasal pillow (i.e. the side that receives the valve cartridge) may remain substantially the same throughout each size embodiment. Additionally the nasal pillow may have a wall thickness that varies. For example, the nasal interface structure thickness may be thinner to allow for a more comfortable and flexible interface with the patient's nostrils, while the other portions of the nasal pillow are made thicker so as to maintain the nasal pillow rigid enough for the headgear assembly to properly connect and maintain the position on the patient.

Any of the suitable technologies and materials set forth and incorporated herein may be used to implement various example aspects of the invention as would be apparent to one of skill in the art.

Although exemplary embodiments and applications of the invention have been described herein including as described above and shown in the included example Figures, there is no intention that the invention be limited to these exemplary embodiments and applications or to the manner in which the exemplary embodiments and applications operate or are described herein. Indeed, many variations and modifications to the exemplary embodiments are possible as would be apparent to a person of ordinary skill in the art. The invention may include any device, structure, method, or functionality, as long as the resulting device, system or method falls within the scope of one of the claims that are allowed by the patent office based on this or any related patent application.

The invention claimed is:

1. A nasal pillow system for treating sleep apnea, the system comprising:
    a removable valve cartridge, comprising an inspiratory valve and an expiratory valve;
    a hose connected to the removable valve cartridge on one end and connected to a blower box on the other end;
    a nasal pillow comprising:
        a cavity wall defining a cavity;
        a valve cartridge receiver opening formed into the cavity wall and constructed to receive the removable valve cartridge;
        two nasal interface structures connected to the cavity wall, wherein each of the nasal interface structures extends from the cavity wall, and wherein each of the nasal interface structures defines an internal air flow channel with a cross-sectional area, the internal air flow channel in fluid communication with the cavity, and each of the nasal interface structures comprises:
            a conical nasal interface adapted to be inserted into a patient's nostril, the conical nasal interface having an opening to the airflow channel;
            a cylindrical trunk structure connected to the conical nasal interface wherein the cross-sectional area at the connection remains substantially constant;
            an annular relief pocket connected to the cylindrical trunk structure and the cavity wall;
            wherein the connection between the annular relief pocket and the cavity wall defines a plane, a first portion of the annular relief pocket extends away from the plane, and a second portion extends toward the plane; and wherein the connection between the cylindrical trunk structure and the conical nasal interface is adapted to maintain the cylindrical trunk structure fixed relative to the conical nasal interface when the nasal pillow is used by a patient.

2. The nasal pillow system of claim 1, wherein the annular relief pocket comprises an annular wall indentation extending into the cavity.

3. The nasal pillow system of claim 1, wherein the annular relief pocket is constructed so as to allow the opening to move toward and away from the plane and in a direction that is parallel to the plane.

4. The nasal pillow system of claim 1, wherein the annular relief pocket defines a cross-sectional area, and when one of the nasal interface structures moves, the cross-sectional area remains substantially constant.

5. The nasal pillow system of claim 1, wherein the nasal pillow is made of silicone.

6. The nasal pillow system of claim 1, wherein the nasal pillow comprises a strap attachment structure.

7. The nasal pillow system of claim 6, wherein the strap attachment structure is a slot or a tab.

8. The nasal pillow system of claim 6, wherein the strap attachment structure is an asymmetrical tab.

9. The nasal pillow system of claim 6, further comprising a headgear assembly attached to the strap attachment structure.

10. The nasal pillow system of claim 6, wherein the cavity wall varies in thickness.

\* \* \* \* \*